(12) United States Patent
Goto et al.

(10) Patent No.: US 11,458,238 B2
(45) Date of Patent: Oct. 4, 2022

(54) BLOOD PURIFICATION APPARATUS

(71) Applicant: Nikkiso Company Limited, Tokyo (JP)

(72) Inventors: Hitoshi Goto, Shizuoka (JP); Masahiro Toyoda, Shizuoka (JP); Tomoya Murakami, Shizuoka (JP); Kunihiko Akita, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 443 days.

(21) Appl. No.: 16/743,189

(22) Filed: Jan. 15, 2020

(65) Prior Publication Data
US 2020/0147291 A1 May 14, 2020

Related U.S. Application Data

(63) Continuation of application No. PCT/JP2018/025578, filed on Jul. 5, 2018.

(30) Foreign Application Priority Data

Jul. 21, 2017 (JP) .............................. JP2017-142027

(51) Int. Cl.
*A61M 1/36* (2006.01)
*A61M 1/16* (2006.01)

(52) U.S. Cl.
CPC ........ *A61M 1/3669* (2013.01); *A61M 1/1601* (2014.02)

(58) Field of Classification Search
CPC .............. A61M 1/3669; A61M 1/1601; A61M 2205/3317; A61M 2205/52; A61M 1/3656
See application file for complete search history.

(56) References Cited

U.S. PATENT DOCUMENTS

| 2003/0194894 A1 | 10/2003 | Wariar et al. |
| 2010/0016809 A1 | 1/2010 | Grober et al. |
| 2017/0173253 A1* | 6/2017 | Funkhouser ........ A61M 1/3656 |

FOREIGN PATENT DOCUMENTS

| EP | 3148608 A2 | 4/2017 |
| JP | 2006-110120 A | 4/2006 |

(Continued)

OTHER PUBLICATIONS

European Search Report for Application No. 18835275.1, dated Mar. 15, 2021.

*Primary Examiner* — Kabir A Timory
(74) *Attorney, Agent, or Firm* — Young Basile Hanlon & MacFarlane, P.C.

(57) ABSTRACT

A blood purification apparatus is provided that is capable of detecting an abnormal state of puncture into a blood vessel with an arterial puncture needle or a venous puncture needle. The blood purification apparatus includes an oscillating device capable of supplying an alternating current at a predetermined frequency and changing the frequency of the alternating current among a plurality of frequencies, a measuring device capable of measuring an impedance for each of the frequencies, a calculating device capable of acquiring an impedance frequency characteristic, a storage device capable of storing an impedance frequency characteristic acquired in a case of normal puncture into the patient's blood vessel with an arterial puncture needle and a venous puncture needle, and an identifying device capable of identifying whether the puncture into the blood vessel with the arterial puncture needle a or the venous puncture needle b is normal in accordance with the change observed between the impedance frequency characteristic acquired by the calculating device and the impedance frequency characteristic stored in the storage device.

8 Claims, 7 Drawing Sheets

(56) References Cited

FOREIGN PATENT DOCUMENTS

| | | |
|---|---|---|
| JP | 2010-012286 A | 1/2010 |
| JP | 2010-155109 A | 7/2010 |
| JP | 2013-022310 A | 2/2013 |
| JP | 2016-158712 A | 9/2016 |
| JP | 2016-158919 A | 9/2016 |
| WO | 2002/102441 A1 | 12/2002 |
| WO | 2003/086506 A1 | 10/2003 |
| WO | 2008/028653 A2 | 3/2008 |

\* cited by examiner

[Fig. 1]
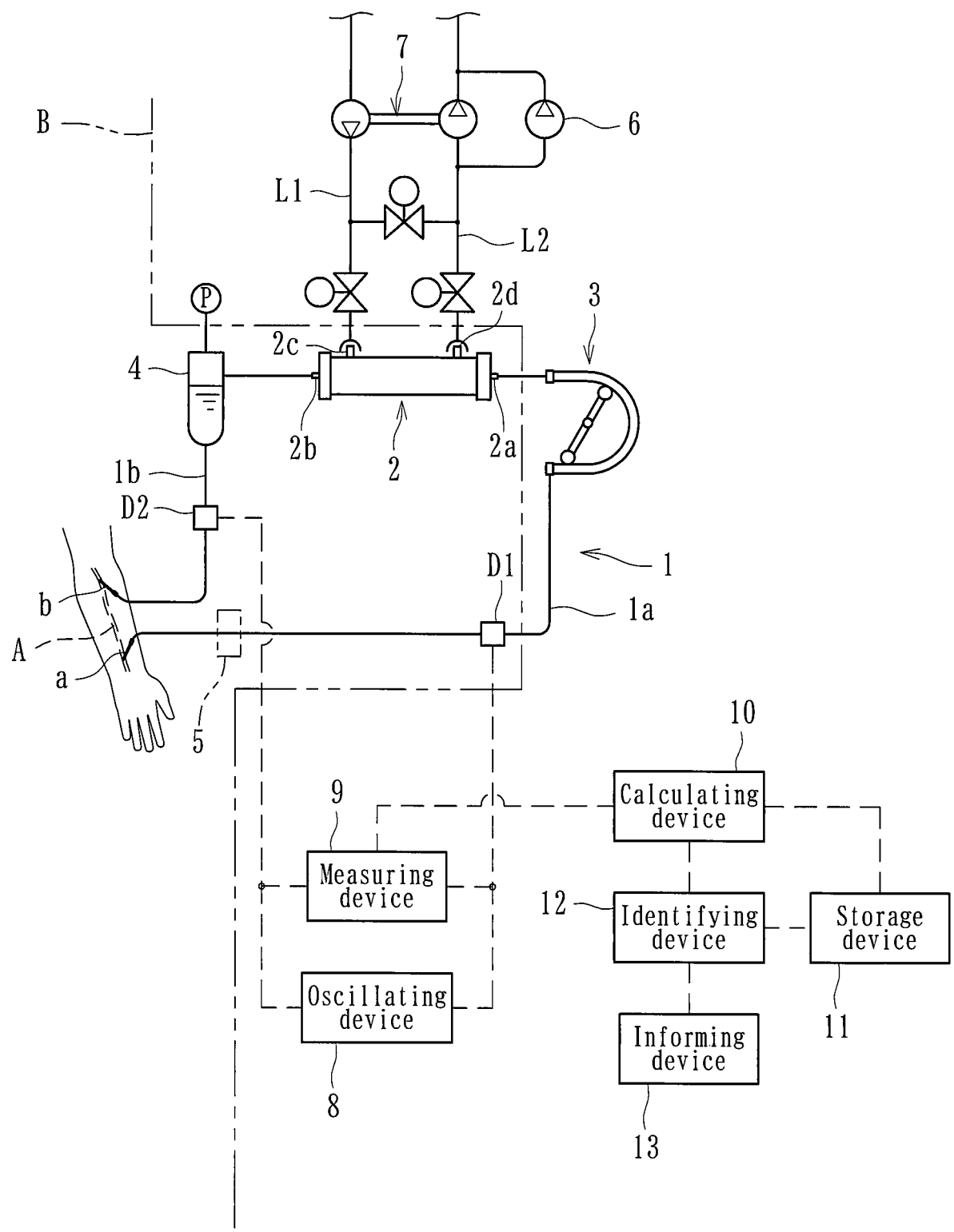

[Fig. 2]
(a)
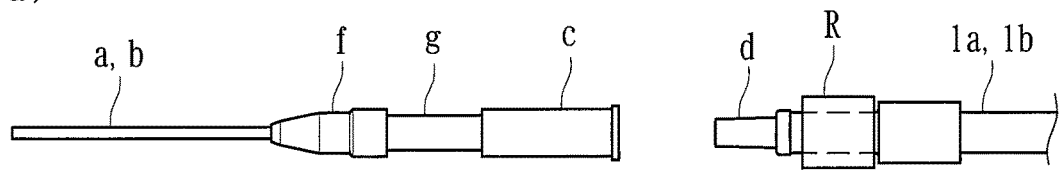
(b)
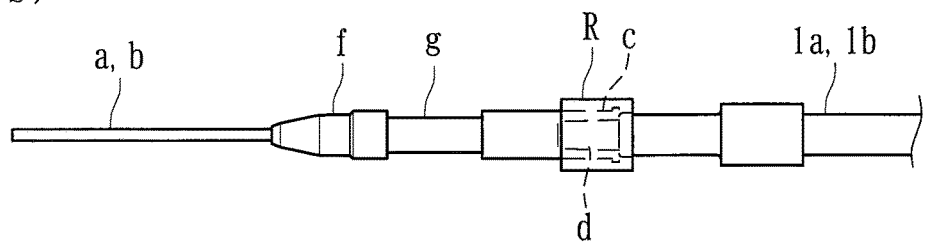
[Fig. 3]
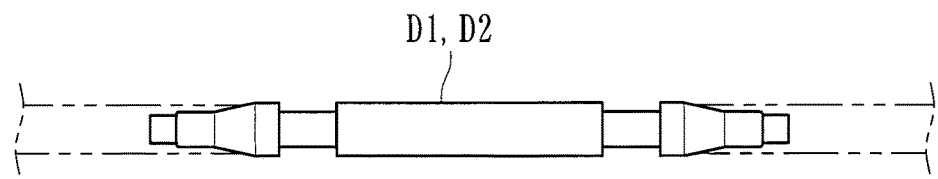
[Fig. 4]
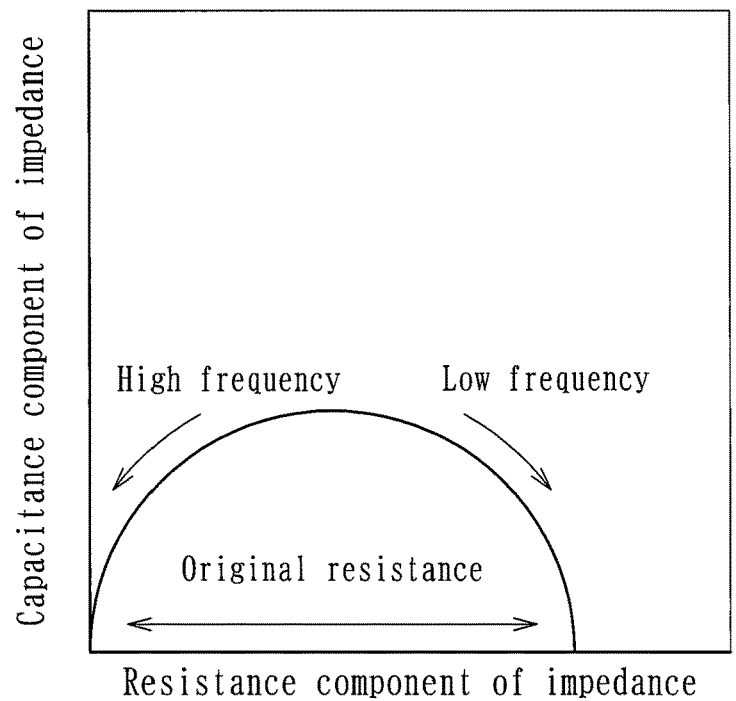

[ Fig. 5 ]
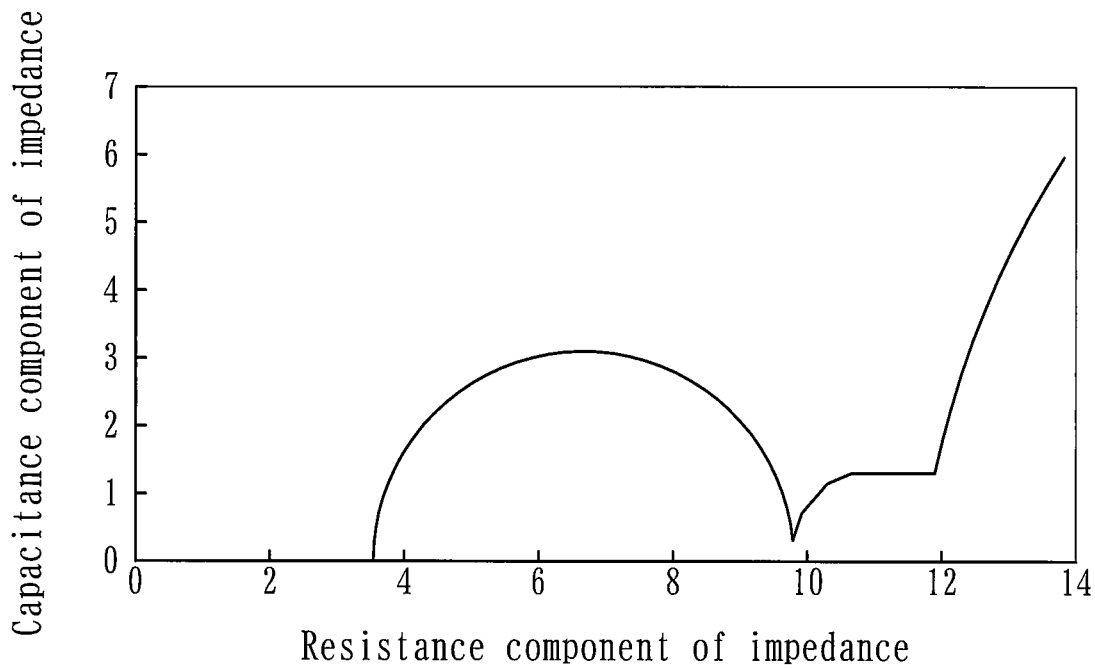
[ Fig. 6 ]
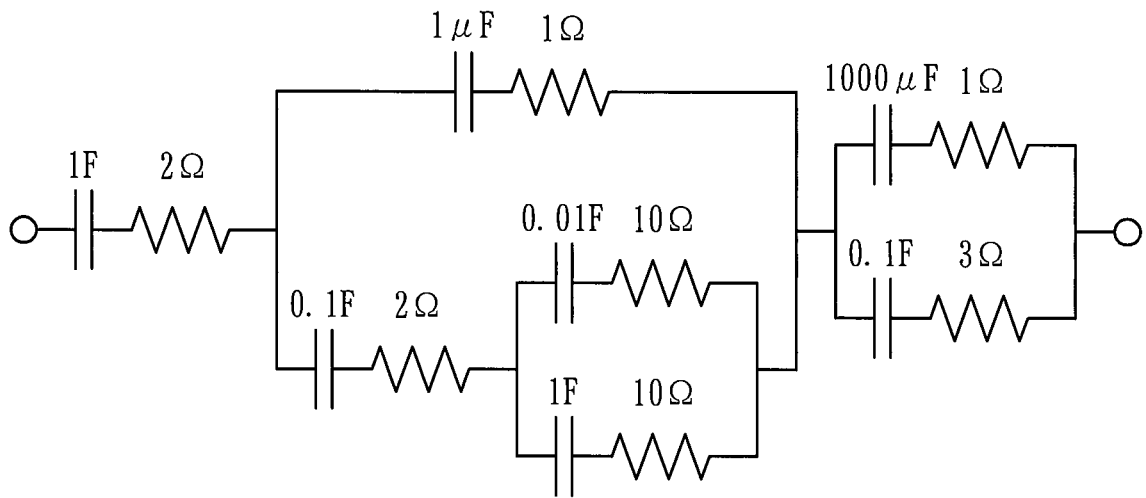

[Fig. 7]
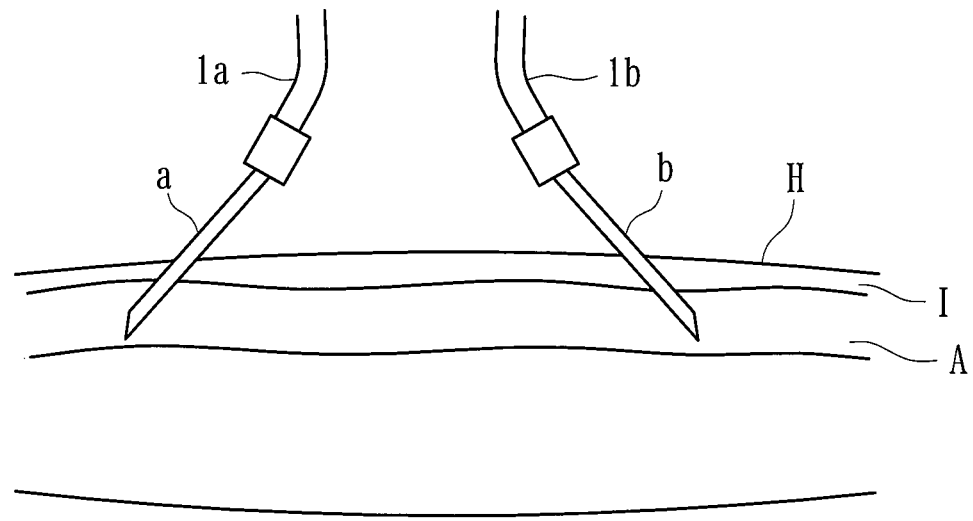
[Fig. 8]
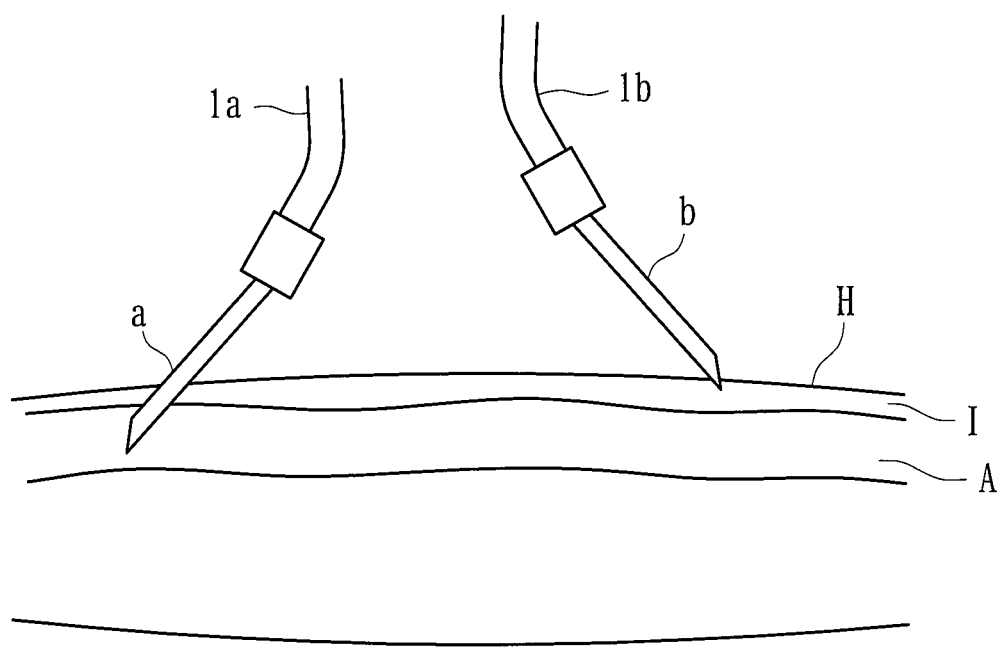

[ Fig. 9 ]
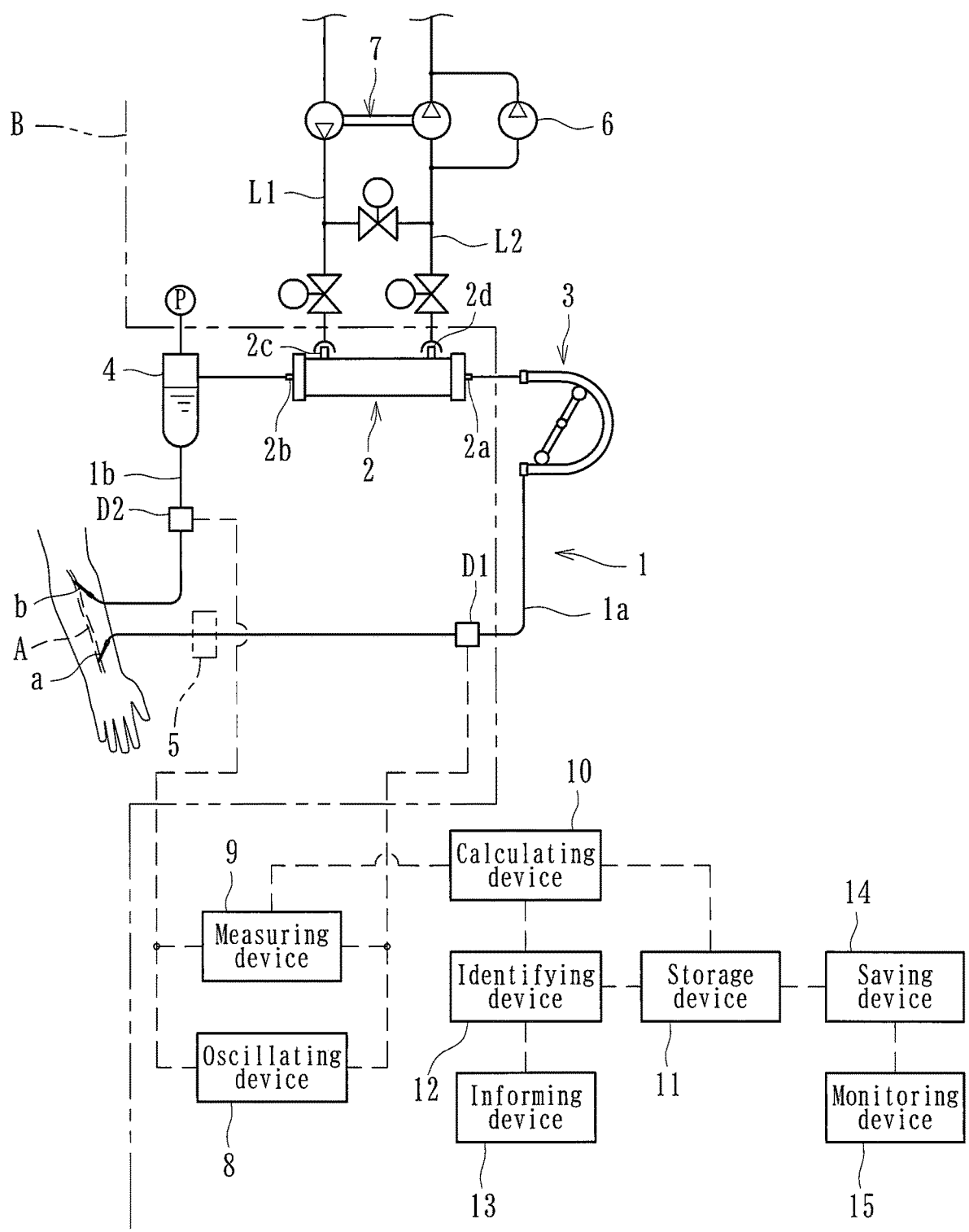

[Fig. 10]
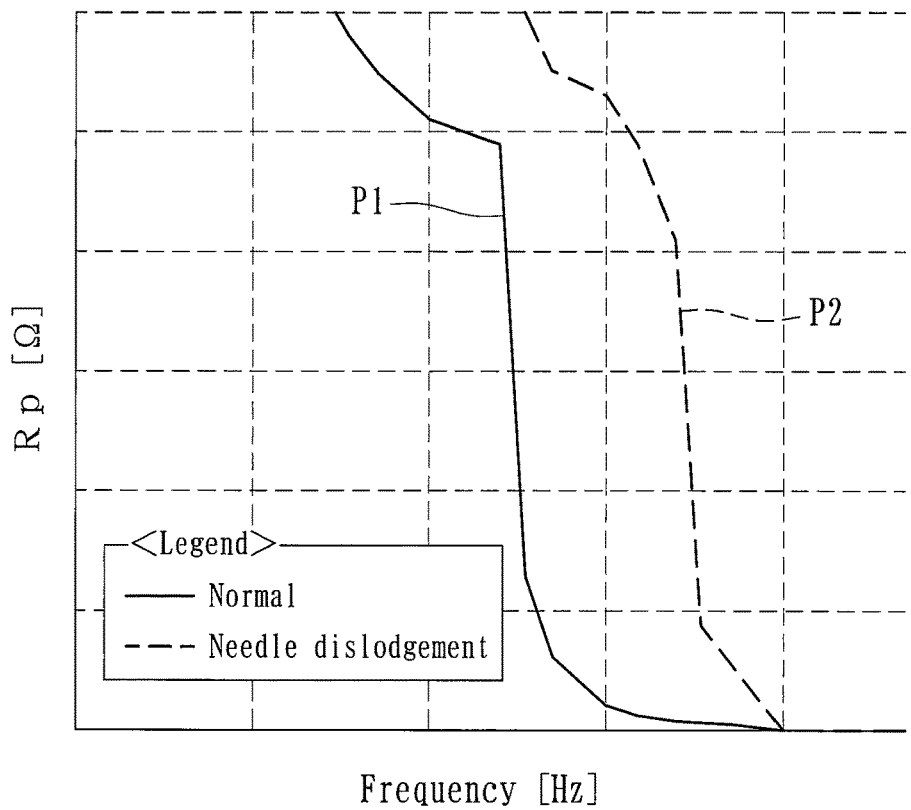
[Fig. 11]
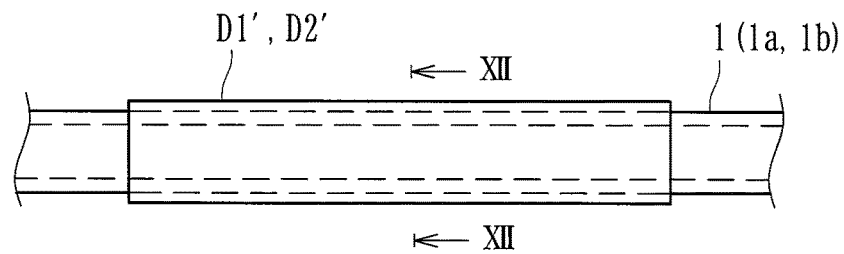
[Fig. 12]
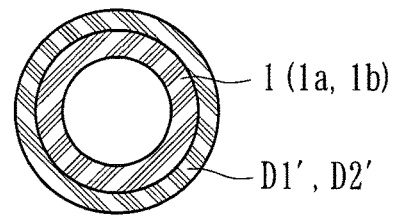
[Fig. 13]
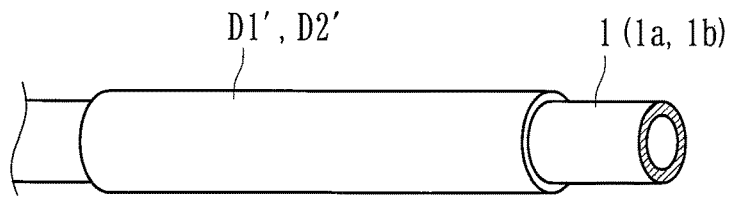

[ Fig. 14 ]
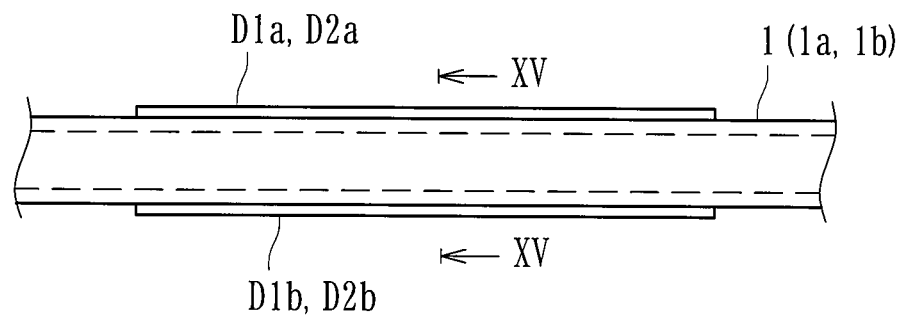
[ Fig. 15 ]
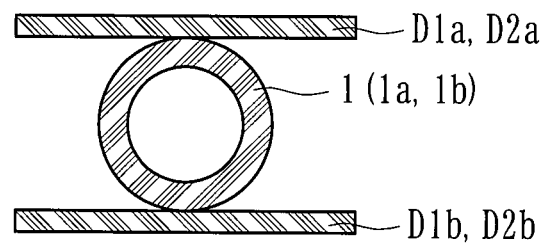

BLOOD PURIFICATION APPARATUS

CROSS-REFERENCE TO RELATED APPLICATION(S)

This application is a continuation of International Application No. PCT/JP2018/025578, filed on Jul. 5, 2018, which claims priority to Japanese Application No. 2017-142027, filed on Jul. 21, 2017, the entire disclosures of which are hereby incorporated by reference.

FIELD

The present invention relates to a blood purification apparatus capable of purifying a patient's blood extracorporeally circulating through an arterial blood circuit and a venous blood circuit.

BACKGROUND

In general, dialysis treatment is performed with a dialysis treatment apparatus including a blood circuit for extracorporeal circulation of a patient's blood, a dialyzer connected to a halfway position of the blood circuit, a peristaltic blood pump, and a dialysis device capable of performing ultrafiltration while performing hemodialysis treatment by introducing and delivering dialysate into and from the dialyzer. Typically, dialysis treatment performed with such a dialysis treatment apparatus is conducted for about four hours every other day. Therefore, the hemodynamics of the patient changes greatly during the treatment. In particular, it is an important issue to effectively and assuredly prevent the reduction in blood pressure due to removal of excessive water (ultrafiltration).

On the other hand, in blood purification treatment, an arterial puncture needle and a venous puncture needle are stuck into the patient, and the patient's blood is collected through the arterial puncture needle and is purified while being caused to extracorporeally circulate through the blood circuit. The purified blood needs to be returned to the patient through the venous puncture needle. While the blood is in extracorporeal circulation, the puncture needles may be accidentally dislodged from the puncture site of the patient because of, for example, a body movement or the like. In particular, if the venous puncture needle is dislodged, the blood may leak to the outside. To detect such dislodgement of the puncture needle, there is a known proposal of a blood purification apparatus capable of identifying a dislodged state of a puncture needle by supplying an alternating current to a blood circuit (see PTL 1 and 2, for example).
PTL 1: Japanese Unexamined Patent Application Publication No. 2010-12286 and PTL 2: Japanese Unexamined Patent Application Publication No. 2010-155109 the teachings of which are expressly incorporated by reference herein for all purposes.

SUMMARY

However, the above known technique has the following problem. Although the state of complete dislodgement of the arterial puncture needle or the venous puncture needle from the patient's body is identifiable, it is impossible to detect a state of the arterial puncture needle or the venous puncture needle that is stuck in the patient's body but is not normally stuck in the blood vessel (an abnormal state of puncture into the blood vessel). Such an abnormal state of puncture into the blood vessel is a sign indicating that the puncture needle may be completely dislodged from the patient's body. Therefore, it is important to identify the abnormal state and let medical workers pay attention to the abnormal state.

The present invention has been conceived in view of the above circumstances and provides a blood purification apparatus capable of detecting an abnormal state of puncture into a blood vessel with an arterial puncture needle or a venous puncture needle.

According to the present teachings, there is provided a blood purification apparatus that has an arterial blood circuit provided with an arterial puncture needle at a distal end, the arterial puncture needle being stickable into a patient; a venous blood circuit provided with a venous puncture needle at a distal end, the venous puncture needle being stickable into the patient; and a blood purification device connected to a proximal end of the arterial blood circuit and to a proximal end of the venous blood circuit and being capable of purifying the patient's blood that extracorporeally circulates through the arterial blood circuit and the venous blood circuit. The blood purification apparatus includes an arterial electrode provided to the arterial blood circuit; a venous electrode provided to the venous blood circuit; an oscillating device capable of supplying, by applying a voltage between the arterial electrode and the venous electrode, an alternating current at a predetermined frequency to the patient's blood through the arterial puncture needle and the venous puncture needle that are stuck in the patient's blood vessel (a vascular access or the like), the oscillating device being capable of changing the frequency of the alternating current among a plurality of frequencies; a measuring device capable of measuring an impedance of a flow route supplied with the alternating current from the oscillating device, the impedance being measured for each of the frequencies; a calculating device capable of acquiring an impedance frequency characteristic based on the impedances measured for the respective frequencies by the measuring device; a storage device capable of storing an impedance frequency characteristic acquired in a case of normal puncture into the patient's blood vessel with the arterial puncture needle and the venous puncture needle; and an identifying device capable of comparing the impedance frequency characteristic acquired by the calculating device and the impedance frequency characteristic stored in the storage device, and identifying whether the puncture into the patient's blood vessel with the arterial puncture needle or the venous puncture needle is normal in accordance with a change in the frequency characteristic.

According to the teachings herein, in the blood purification apparatus taught herein, the oscillating device is capable of changing the frequency of the alternating current between a low frequency and a high frequency.

According to the teachings herein, in the blood purification apparatus taught herein, the storage device is capable of storing the impedance frequency characteristic acquired by the calculating device after the patient's blood is introduced into the arterial blood circuit and the venous blood circuit and before blood purification treatment is started.

According to the teachings herein, in the blood purification apparatus taught herein, the supply of the alternating current from the oscillating device with the frequency changed among the plurality of frequencies, the acquisition of the impedance frequency characteristic by the calculating device, and the identification by the identifying device are each performed continuously or intermittently from a start to an end of the blood purification treatment.

According to the teachings herein, the blood purification apparatus taught herein further includes a saving device capable of successively storing the impedance frequency characteristic stored in the storage device for each session of blood purification treatment and saving the stored impedance frequency characteristic as past impedance-frequency-characteristic data; and a monitoring device capable of comparing the past impedance-frequency-characteristic data saved in the saving device and an impedance frequency characteristic of a current session of blood purification treatment that is stored in the storage device, and monitoring any change in the frequency characteristic.

According to the teachings herein, the blood purification apparatus taught herein further includes an informing device that informs a result of the identification by the identifying device that the puncture into the blood vessel with the arterial puncture needle or the venous puncture needle is abnormal.

According to the teachings herein, in the blood purification apparatus taught herein, the identifying device is capable of comparing a frequency characteristic defined by a resistance component alone of the impedance acquired by the calculating device and a frequency characteristic defined by a resistance component alone of the impedance stored in the storage device, and identifying whether the puncture into the patient's blood vessel with the arterial puncture needle or the venous puncture needle is normal in accordance with the change in the frequency characteristic.

According to the teachings herein, in the blood purification apparatus taught herein, the arterial electrode and the venous electrode are each an electrode formed in contact with an outer peripheral surface of a flexible tube forming a corresponding one of the arterial blood circuit and the venous blood circuit, and each allow the voltage to be non-wettably applied to liquid flowing in the corresponding one of the arterial blood circuit and the venous blood circuit.

According to the teachings herein, whether the puncture into the patient's blood vessel with the arterial puncture needle or the venous puncture needle is normal can be identified in accordance with the change in the impedance frequency characteristic. Therefore, the abnormal state of puncture into the blood vessel with the arterial puncture needle or the venous puncture needle can be detected.

According to the teachings herein, the oscillating device is capable of changing the frequency of the alternating current between a low frequency and a high frequency. Therefore, impedance frequency characteristics for a wide range of frequencies can be acquired. Accordingly, the abnormal state of puncture into the blood vessel with the arterial puncture needle or the venous puncture needle can be identified accurately.

According to the teachings herein, the storage device is capable of storing the impedance frequency characteristic acquired by the calculating device after the patient's blood is introduced into the arterial blood circuit and the venous blood circuit and before blood purification treatment is started. Therefore, any change in the impedance frequency characteristic that may occur during the blood purification treatment can be detected assuredly. Hence, the identifying device can make the identification correctly.

According to the teachings herein, the supply of the alternating current from the oscillating device with the frequency changed among the plurality of frequencies, the acquisition of the impedance frequency characteristic by the calculating device, and the identification by the identifying device are each performed continuously or intermittently from the start to the end of the blood purification treatment. Therefore, the abnormal state of puncture into the blood vessel with the arterial puncture needle or the venous puncture needle can be assuredly identified during the blood purification treatment.

According to the teachings herein, the blood purification apparatus includes the saving device capable of successively storing the impedance frequency characteristic stored in the storage device for each session of blood purification treatment and saving the stored impedance frequency characteristic as past impedance-frequency-characteristic data; and the monitoring device capable of comparing the past impedance-frequency-characteristic data saved in the saving device and the impedance frequency characteristic of the current session of blood purification treatment that is stored in the storage device, and monitoring any change in the frequency characteristic. Therefore, the state of vascular access to the patient (the patient's blood vessel A illustrated in FIGS. 7, 8, and others) can be monitored, and any abnormal state of puncture into the blood vessel with the arterial puncture needle or the venous puncture needle that may occur before the current session of blood purification treatment is started can be identified.

According to the teachings herein, the blood purification apparatus includes the informing device that informs the result of the identification by the identifying device that the puncture into the blood vessel with the arterial puncture needle or the venous puncture needle is abnormal. Therefore, medical workers or the like nearby can immediately know the abnormal state of puncture into the blood vessel with the arterial puncture needle or the venous puncture needle and can immediately take an action to such a situation.

According to the teachings herein, the identifying device is capable of comparing the frequency characteristic defined by the resistance component alone of the impedance acquired by the calculating device and the frequency characteristic defined by the resistance component alone of the impedance stored in the storage device, and identifying whether the puncture into the patient's blood vessel with the arterial puncture needle or the venous puncture needle is normal in accordance with the change in the frequency characteristic. Therefore, the abnormal state of puncture into the blood vessel with the arterial puncture needle or the venous puncture needle can be easily identified in accordance with the resistance component alone.

According to the teachings herein, the arterial electrode and the venous electrode are each an electrode formed in contact with the outer peripheral surface of the flexible tube forming a corresponding one of the arterial blood circuit and the venous blood circuit, and each allow the voltage to be non-wettably applied to the liquid flowing in the corresponding one of the arterial blood circuit and the venous blood circuit. Hence, there is no need to attach the electrode on the blood flow route in each of the arterial blood circuit and the venous blood circuit. Accordingly, the blood flow route is prevented from having surface irregularities for attaching the electrode. Therefore, smooth flow of the blood can be maintained. Furthermore, since the voltage can be non-wettably applied to the blood, an electrode made of metal, which has low biocompatibility, can be employed.

BRIEF DESCRIPTION OF THE DRAWINGS

FIG. 1 is an overall diagram illustrating a blood purification apparatus according to an embodiment of the present invention.

FIG. 2 includes diagrams illustrating a puncture needle (one of an arterial puncture needle and a venous puncture needle) included in the blood purification apparatus.

FIG. 3 is a diagram illustrating an electrode (an arterial electrode or a venous electrode) included in the blood purification apparatus.

FIG. 4 is a graph illustrating an impedance frequency characteristic stored in a storage device included in the blood purification apparatus.

FIG. 5 is a graph illustrating an impedance frequency characteristic acquired by a calculating device included in the blood purification apparatus in a case of abnormal puncture into a blood vessel with the puncture needles.

FIG. 6 is a diagram illustrating an equivalent circuit that exhibits the impedance frequency characteristic illustrated in FIG. 5.

FIG. 7 is a diagram illustrating a normal state of puncture into the blood vessel with the arterial puncture needle and the venous puncture needle of the blood purification apparatus.

FIG. 8 is a diagram illustrating an abnormal state of puncture into the blood vessel with the arterial puncture needle or the venous puncture needle (in the illustrated case, the venous puncture needle) of the blood purification apparatus.

FIG. 9 is an overall diagram illustrating a blood purification apparatus according to another embodiment of the present invention.

FIG. 10 is a graph illustrating a frequency characteristic defined by a resistance component alone of an impedance stored in a storage device of a blood purification apparatus according to yet another embodiment of the present invention, and a frequency characteristic defined by a resistance component alone of an impedance acquired by a calculating device of the blood purification apparatus in the case of abnormal puncture into the blood vessel with the puncture needles.

FIG. 11 is a side view of an electrode (an arterial electrode or a venous electrode) of another type included in the blood purification apparatus.

FIG. 12 is a sectional view taken along line XII-XII illustrated in FIG. 11.

FIG. 13 is a perspective view of the electrode (the arterial electrode or the venous electrode) of the another type.

FIG. 14 is a side view of an electrode (an arterial electrode or a venous electrode) of yet another type included in the blood purification apparatus.

FIG. 15 is a sectional view taken along line XV-XV illustrated in FIG. 14.

DETAILED DESCRIPTION

Embodiments of the present invention will now be described specifically with reference to the drawings.

A blood purification apparatus according to an embodiment is a hemodialysis apparatus intended for hemodialysis treatment and ultrafiltration that are performed while a patient's blood is caused to extracorporeally circulate. As illustrated in FIG. 1, the blood purification apparatus includes a blood circuit 1, and a dialyzer 2 as a blood purification device connected to the blood circuit 1. The blood purification apparatus further includes, in an apparatus body B, a dialysate introduction line L1 and a dialysate drain line L2, an arterial electrode D1 and a venous electrode D2, an oscillating device 8, a measuring device 9, a calculating device 10, a storage device 11, an identifying device 12, and an informing device 13.

The blood circuit 1 is formed of a flexible tube through which fluid such as blood is allowed to flow. The blood circuit 1 includes an arterial blood circuit 1a and a venous blood circuit 1b. The arterial (blood-removal or blood-collection) blood circuit 1a is provided with an arterial puncture needle a (see FIGS. 1 and 2) connectable to a distal end thereof, and with a peristaltic blood pump 3 at a halfway position thereof. The venous (blood-returning) blood circuit 1b is provided with a venous puncture needle b (see FIGS. 1 and 2) connected to a distal end thereof, and with an air-trap chamber 4 for bubble removal at a halfway position thereof. In this specification, the side of the puncture needle provided for blood removal (blood collection) is referred to as the "arterial" side, and the side of the puncture needle provided for blood return is referred to as the "venous" side. The "arterial" side and the "venous" side are not defined in accordance with which of the artery and the vein is to be the object of puncture.

The arterial puncture needle a and the venous puncture needle b according to the present embodiment are each a puncture needle (an accessing device) that is stickable into a patient. As illustrated in FIG. 2, the arterial puncture needle (a) and the venous puncture needle (b) are each a cannula (an intravascular indwelling needle) attached to a distal part f made of rigid resin or the like. The distal part (f) is connected to a joint (c), which is made of rigid resin or the like, through a clamping flexible tube (g). As illustrated in part (a) of the drawing, the distal part (f), the clamping flexible tube (g), and the joint (c) are integrated into a unit.

The distal end of the arterial blood circuit 1a and the distal end of the venous blood circuit 1b each have a joint (d) made of rigid resin or the like. As illustrated in part (b) of the drawing, the joint c on the puncture-needle side is fitted onto the joint d and is screwed thereto with a lock ring R, whereby the fitted state can be locked. If the clamping flexible tube (g) is clamped with a clamp, the flow route between the arterial puncture needle a or the venous puncture needle (b) and the arterial blood circuit 1a or the venous blood circuit 1b can be closed.

When the blood pump 3 is activated with the arterial puncture needle (a) and the venous puncture needle (b) being stuck in the patient, the patient's blood that is collected through the arterial puncture needle a flows through the arterial blood circuit 1a and reaches the dialyzer 2, where the blood is purified. Then, the blood flows through the venous blood circuit 1b with bubbles therein being removed in the air-trap chamber 4, and returns into the patient's body through the venous puncture needle (b). Thus, the patient's blood can be purified by the dialyzer 2 while extracorporeally circulating through the blood circuit 1.

The dialyzer 2 has, in a housing thereof, a blood introduction port 2a, a blood delivery port 2b, a dialysate introduction port 2c, and a dialysate delivery port 2d. The blood introduction port 2a receives a proximal end of the arterial blood circuit 1a that is connected thereto. The blood delivery port 2b receives a proximal end of the venous blood circuit 1b that is connected thereto. The dialysate introduction port 2c and the dialysate delivery port 2d are connected to the dialysate introduction line L1 and the dialysate drain line L2, respectively, extending from the apparatus body B.

The housing of the dialyzer 2 houses a plurality of hollow fibers. The inside of each of the hollow fibers serves as a blood flow route. The space between the outer peripheral surface of each of the hollow fibers and the inner peripheral surface of the housing serves as a dialysate flow route. The hollow fibers each have a number of very small holes (pores) extending therethrough from the outer peripheral surface to the inner peripheral surface, thereby forming a hollow fiber membrane. Impurities and the like contained in the blood are allowed to penetrate through the membranes into the dialysate.

As illustrated in FIG. 1, the apparatus body B includes a duplex pump 7 provided over the dialysate introduction line L1 and the dialysate drain line L2, and an ultrafiltration pump 6 connected to a bypass line connected to the dialysate drain line L2 in such a manner as to bypass the duplex pump 7. One end of the dialysate introduction line L1 is connected to the dialyzer 2 (the dialysate introduction port 2c), and the other end is connected to a dialysate supply device (not illustrated) that prepares a dialysate at a predetermined concentration. One end of the dialysate drain line L2 is connected to the dialyzer 2 (the dialysate delivery port 2d), and the other end is connected to a drainage device (not illustrated). The dialysate supplied from the dialysate supply device flows through the dialysate introduction line L1 into the dialyzer 2, and then flows through the dialysate drain line L2 into the drainage device.

The ultrafiltration pump 6 is provided for removing water from the patient's blood flowing through the dialyzer 2. Specifically, when the ultrafiltration pump 6 is activated, the amount of liquid drained through the dialysate drain line L2 becomes greater than the amount of dialysate introduced through the dialysate introduction line L1. Hence, water is removed from the blood by an amount corresponding to the excess. Water may be removed from the patient's blood with another device (such as a device employing a so-called balancing chamber or the like) instead of the duplex pump 7.

A bubble detection device 5 is a sensor capable of detecting bubbles (air) flowing in the flexible tube forming the arterial blood circuit 1a. The bubble detection device 5 includes, for example, an ultrasonic vibrator formed of a piezoelectric device, and an ultrasonic receiver formed of a piezoelectric device. The bubble detection device 5 is capable of emitting ultrasonic waves from the ultrasonic vibrator toward the flexible tube forming the arterial blood circuit 1a, and is also capable of receiving the thus generated vibration by the ultrasonic receiver.

The ultrasonic receiver is configured to generate a voltage that changes with the vibration received. The ultrasonic receiver is capable of detecting the flow of bubbles by a fact that the detected voltage has exceeded a predetermined threshold. Specifically, the ultrasonic attenuation factor of bubbles is higher than those of blood and substitution solutions. Hence, the ultrasonic waves transmitted through the liquid are detected. Then, if the detected voltage has exceeded the predetermined threshold, it is regarded that the flow of bubbles (gas) has been detected.

The present embodiment employs the arterial electrode D1 and the venous electrode D2. The arterial electrode D1 is an electrode attached to the arterial blood circuit 1a (between a position where the blood pump 3 is provided and the arterial puncture needle a). The venous electrode D2 is an electrode attached to the venous blood circuit 1b (between a position where the air-trap chamber 4 is provided and the venous puncture needle (b)).

As illustrated in FIG. 3, the arterial electrode D1 and the venous electrode D2 are each a conductive member connected to a corresponding one of the flexible tubes and are each electrically connected to the oscillating device 8 with a connecting device such as an alligator clip. Hence, a predetermined voltage can be applied to the blood flowing therethrough. The arterial electrode D1 and the venous electrode D2 are each not limited to the one illustrated in FIG. 3 and may each be a device of any other type (including a device that does not directly come into contact with blood), as long as the device is capable of applying the voltage from the oscillating device 8 to the blood flowing in a corresponding one of the arterial blood circuit 1a and the venous blood circuit 1b.

Electrodes that do not directly come into contact with blood include an arterial electrode D1' and a venous electrode D2' illustrated in FIGS. 11 to 13. The arterial electrode D1' and the venous electrode D2' are each, for example, a cylindrically formed metal pipe (such as a stainless pipe), a pipe made of conductive rubber or conductive plastic, or the like. The arterial electrode D1' and the venous electrode D2' are each provided in contact with the outer peripheral surface of the flexible tube forming a corresponding one of the arterial blood circuit 1a and the venous blood circuit 1b, and each allow a voltage to be non-wettably applied to the liquid flowing in the arterial blood circuit 1a or the venous blood circuit 1b.

Other electrodes that do not directly come into contact with blood include an arterial electrode (D1a and D1b) and a venous electrode (D2a and D2b) illustrated in FIGS. 14 and 15. The arterial electrode (D1a and D1b) and the venous electrode (D2a and D2b) are each, for example, a pair of plate-shaped electrodes that are provided in contact with the outer peripheral surface of the flexible tube forming a corresponding one of the arterial blood circuit 1a and the venous blood circuit 1b in such a manner as to hold the flexible tube therebetween. The arterial electrode (D1a and D1b) and the venous electrode (D2a and D2b) each allow a voltage to be non-wettably applied to the liquid flowing in the arterial blood circuit 1a or the venous blood circuit 1b. Such an electrode has a simple configuration and can be easily applied to flexible tubes having various outside diameters.

As described above, the arterial electrode (D1' or D1a and D1b) and the venous electrode (D2' or D2a and D2b) are each an electrode formed in contact with the outer peripheral surface of the flexible tube forming a corresponding one of the arterial blood circuit 1a and the venous blood circuit 1b and each allow a voltage to be non-wettably applied to the liquid flowing in the arterial blood circuit 1a or the venous blood circuit 1b. Hence, there is no need to attach the electrode on the blood flow route in each of the arterial blood circuit 1a and the venous blood circuit 1b. Accordingly, the blood flow route is prevented from having surface irregularities for attaching the electrode. Therefore, smooth flow of the blood can be maintained. Furthermore, since the voltage can be non-wettably applied to the blood, an electrode made of metal, which has low biocompatibility, can be employed.

The arterial electrode (D1' or D1a and D1b) and the venous electrode (D2' or D2a and D2b) may be bonded to or detachable from the arterial blood circuit 1a and the venous blood circuit 1b, respectively. If detachable, the arterial electrode (D1' or D1a and D1b) and the venous electrode (D2' or D2a and D2b) can be used for a plurality of treatment sessions, leading to a cost reduction.

The oscillating device 8 is capable of supplying, by applying a voltage between the arterial electrode D1 and the venous electrode D2, an alternating current at a predetermined frequency to the patient's blood through the arterial puncture needle a and the venous puncture needle b that are stuck in the patient's blood vessel. The oscillating device 8 is also capable of changing the frequency of the alternating current among a plurality of frequencies. More specifically, the oscillating device 8 is connected to the arterial electrode D1 and to the venous electrode D2 through respective wires and is capable of supplying an alternating current thereto while changing the frequency of the alternating current between a low frequency (for example, several tens of hertz) and a high frequency (for example, several megahertz).

The measuring device 9 is connected to the wires that electrically connect the oscillating device 8 to the arterial electrode D1 and to the venous electrode D2, respectively. The measuring device 9 is capable of measuring, for each of the different frequencies, the impedance of the flow route supplied with the alternating current from the oscillating device 8 (the flow route formed between the arterial electrode D1 and the venous electrode D2 through the arterial puncture needle a and the venous puncture needle (b)). The measuring device 9 may be connected to any other position, as long as the measuring device 9 is capable of measuring, for each of the different frequencies, the impedance of the flow route supplied with the alternating current from the oscillating device 8.

The calculating device 10 is an arithmetic circuit or the like electrically connected to the measuring device 9 and is capable of acquiring an impedance frequency characteristic based on the impedances measured for the respective frequencies by the measuring device 9. The impedance frequency characteristic acquired by the calculating device 10 is provided as an impedance distribution representing a relationship between a set of resistance components of the respective impedance and a set of capacitance components of the respective impedance.

For example, as illustrated in FIG. 7, if a blood vessel A (a vascular access or the like) is normally punctured with the arterial puncture needle a and the venous puncture needle b, the blood alone is considered to act as a conductor. That is, the electrodes and the blood produce an impedance. In such a case, when the impedance of the flow route supplied with the alternating current from the oscillating device 8 is measured for each of the different frequencies and is plotted sequentially for those frequencies, with the resistance component of the impedance taken on the horizontal axis and the capacitance component of the impedance taken on the vertical axis, an impedance distribution (i.e. an impedance frequency characteristic) illustrated in FIG. 4, for example, can be acquired.

On the other hand, as illustrated in FIG. 8, if the blood vessel A (the vascular access or the like) is not normally punctured with one of or both of the arterial puncture needle (a) and the venous puncture needle (b) (in the illustrated case, only the venous puncture needle (b)) (that is, if the puncture needle is kept stuck in the patient's body but is not normally stuck in the blood vessel A), tissues (such as skin H, subcutaneous tissues I, muscles, or the like illustrated in the drawing) other than blood or any other member (such as gauze or tape) for fixing the puncture needle is also considered to act as a conductor. Hence, the impedance contains various components and is therefore complicated.

In such a case, when the impedance of the flow route supplied with the alternating current from the oscillating device 8 is measured for each of the different frequencies and is plotted sequentially for those frequencies, with the resistance component of the impedance taken on the horizontal axis and the capacitance component of the impedance taken on the vertical axis, an impedance distribution (i.e. an impedance frequency characteristic) illustrated in FIG. 5, for example, can be acquired. An exemplary equivalent circuit that produces the impedance distribution (the impedance frequency characteristic) illustrated in FIG. 5 is illustrated in FIG. 6.

The storage device 11 is capable of storing the impedance frequency characteristic in the case illustrated in FIG. 7 where the patient's blood vessel A is normally punctured with the arterial puncture needle (a) and the venous puncture needle (b). The storage device 11 according to the present embodiment is electrically connected to the calculating device 10 and is capable of storing the impedance frequency characteristic acquired by the calculating device 10 after the patient's blood is introduced into the arterial blood circuit 1a and the venous blood circuit 1b (after blood removal) and before the blood purification treatment is started.

That is, the storage device 11 is configured such that the impedance frequency characteristic acquired by the calculating device 10 after the patient's blood is introduced into the arterial blood circuit 1a and the venous blood circuit 1b (after blood removal) and before the blood purification treatment is started is stored as an impedance frequency characteristic in the case of normal puncture into the patient's blood vessel A with the arterial puncture needle a and the venous puncture needle (b).

The identifying device 12 is electrically connected to the calculating device 10 and to the storage device 11. The identifying device 12 is capable of comparing the impedance frequency characteristic acquired by the calculating device 10 and the impedance frequency characteristic stored in the storage device 11, and identifying whether the puncture into the patient's blood vessel with the arterial puncture needle (a) or the venous puncture needle (b) (one of or both of the arterial puncture needle (a) and the venous puncture needle (b)) is normal in accordance with the change in the frequency characteristic.

Specifically, if the blood vessel A is normally punctured with the arterial puncture needle (a) and the venous puncture needle (b) as illustrated in FIG. 7 before the blood purification treatment but the puncture into the blood vessel A with one of or both of the arterial puncture needle a and the venous puncture needle b becomes abnormal as illustrated in FIG. 8 during the blood purification treatment, the impedance frequency characteristic acquired by the calculating device 10 changes from the initial distribution illustrated in FIG. 4 to, for example, the distribution illustrated in FIG. 5. If it is identified that the change has exceeded a certain level, the puncture into the blood vessel with the arterial puncture needle (a) or the venous puncture needle (b) is identified to be abnormal.

If the puncture into the blood vessel A with the arterial puncture needle (a) and the venous puncture needle (b) is normal during the blood purification treatment, the impedance frequency characteristic acquired by the calculating device 10 shows little change from the initial distribution illustrated in FIG. 4. Therefore, the puncture into the blood vessel A with the arterial puncture needle (a) and the venous puncture needle (b) is identified to be normal. If the arterial puncture needle (a) and the venous puncture needle (b) are completely dislodged from the patient's body during the blood purification treatment, the measuring device 9 cannot measure the impedance. Accordingly, the calculating device 10 cannot acquire the impedance frequency characteristic. On the basis of such a situation, the identifying device 12 can identify the occurrence of needle dislodgement.

The identifying device 12 may employ another identification method in which correlation between the resistance component and the capacitance component of the impedance frequency characteristic is utilized. An example of such a method is as follows.

Letting the resistance component be R, the capacitance component be C, the frequency at the time of measurement be (x), the resistance component of the frequency characteristic in the case of normal puncture into the blood vessel A be Rref(x), the capacitance component of the frequency characteristic in the case of normal puncture be Cref(x), the resistance component of a comparative frequency characteristic be Rcur(x), and the capacitance component of the comparative frequency characteristic be Ccur(x), the following mathematical expressions can be obtained, where a and b denote the lowest one and the highest one, respectively, of available frequencies:

[Mathematical 1]

$$R = \sum_{x=a}^{b} |R_{ref}(x) - R_{cur}(x)|  \quad \text{(Expression 1)}$$

[Mathematical 2]

$$C = \sum_{x=a}^{b} |C_{ref}(x) - C_{cur}(x)|  \quad \text{(Expression 2)}$$

As the value of R obtained through Expression 1 and the value of C obtained through Expression 2 each become closer to 0, it is identified that the frequency characteristic in the case of normal puncture and the frequency characteristic in the comparative case become more approximate to each other (that is, the frequency characteristic shows little change). Accordingly, the state of puncture into the blood vessel A in the comparative case is identified to be normal. If one of or both of R obtained through Expression 1 and C obtained through Expression 2 exceed a predetermined threshold, it is identified that the frequency characteristic in the case of normal puncture and the frequency characteristic in the comparative case are not approximate to each other (that is, the frequency characteristic shows some change). Accordingly, the state of puncture into the blood vessel A in the comparative case is identified to be abnormal.

The identification method employed by the identifying device 12 is not limited to the above. For example, another pattern matching or the like may be employed in which the frequency characteristic in the case of normal puncture and the frequency characteristic in the comparative case can be compared with each other. The present embodiment concerns a case where a distribution (a graph) representing the impedance frequency characteristic is obtained by sequentially plotting the resistance component of the impedance on the horizontal axis and the capacitance component of the impedance on the vertical axis for each of different frequencies. Alternatively, for example, a distribution representing the impedance frequency characteristic may be obtained by sequentially plotting the resistance component of the impedance on the vertical axis and the capacitance component of the impedance on the horizontal axis for each of different frequencies, and pattern matching of such distributions may be performed for the identification by the identifying device 12.

In the present embodiment, the supply of an alternating current by the oscillating device 8 with the frequency changed among a plurality of frequencies, the acquisition of the impedance frequency characteristic by the calculating device 10, and the identification by the identifying device 12 are each performed continuously or intermittently from the start to the end of the blood purification treatment. Therefore, the abnormal state of puncture into the blood vessel with the arterial puncture needle (a) or the venous puncture needle (b) can be assuredly identified during the blood purification treatment.

The informing device 13 informs the result of the identification by the identifying device 12 that the puncture into the blood vessel A with the arterial puncture needle (a) or the venous puncture needle (b) is abnormal. The informing device 13 lets medical workers nearby know the abnormal state of puncture into the blood vessel A with the arterial puncture needle (a) or the venous puncture needle (b) through a predetermined informing scheme (for example, by displaying the information on a monitor or the like, generating a voice or a sound effect, or causing a warning lamp to be turned on or blink).

The informing device 13 provides not only the information that the puncture into the blood vessel A with the arterial puncture needle (a) or the venous puncture needle (b) is abnormal (the puncture needle is kept stuck in the patient's body but is not normally stuck in the blood vessel A) but also information that the arterial puncture needle (a) or the venous puncture needle (b) has been completely dislodged from the patient's body. Thus, the informing device 13 can provide not only the information on the dislodgement of the arterial puncture needle (a) or the venous puncture needle (b) from the patient's body but also information on a sign of dislodgement of the arterial puncture needle (a) or the venous puncture needle (b) from the patient's body.

According to the above embodiment, whether the puncture into the blood vessel A with the arterial puncture needle (a) or the venous puncture needle (b) is normal can be identified in accordance with the change in the impedance frequency characteristic. Therefore, the abnormal state of puncture into the blood vessel A with the arterial puncture needle (a) or the venous puncture needle (b) can be detected. In particular, the oscillating device 8 according to the present embodiment is capable of changing the frequency of the alternating current between a low frequency and a high frequency. Therefore, impedance frequency characteristics for a wide range of frequencies can be acquired. Accordingly, the abnormal state of puncture into the blood vessel A with the arterial puncture needle (a) or the venous puncture needle (b) can be identified accurately.

The storage device 11 according to the present embodiment is capable of storing the impedance frequency characteristic acquired by the calculating device 10 after the patient's blood is introduced into the arterial blood circuit 1a and the venous blood circuit 1b and before the blood purification treatment is started. Therefore, any change in the impedance frequency characteristic that may occur during the blood purification treatment can be detected assuredly. Hence, the identifying device 12 can make the identification correctly.

The present embodiment employs the informing device 13 that informs the result of the identification by the identifying device 12 that the puncture into the blood vessel A with the arterial puncture needle (a) or the venous puncture needle (b) is abnormal. Therefore, medical workers or the like nearby can immediately know the abnormal state of puncture into the blood vessel A with the arterial puncture needle (a) or the venous puncture needle (b) and can immediately take an action to such a situation.

Now, another embodiment of the present invention will be described.

As with the case of the above embodiment, a blood purification apparatus according to the present embodiment is a hemodialysis apparatus intended for hemodialysis treatment and ultrafiltration that are performed while a patient's blood is caused to extracorporeally circulate. As illustrated in FIG. 9, the blood purification apparatus includes a blood circuit 1, and a dialyzer 2 as a blood purification device. The blood purification apparatus further includes, in an apparatus body B, a dialysate introduction line L1 and a dialysate drain line L2, an arterial electrode D1 and a venous electrode D2, an oscillating device 8, a measuring device 9, a calculating device 10, a storage device 11, an identifying device 12, an informing device 13, a saving device 14, and a monitoring device 15. Elements that are the same as those described in the above embodiment are denoted by corresponding ones of the reference numerals, and detailed description of such elements is omitted.

The saving device 14 is electrically connected to the storage device 11 and is capable of successively storing the impedance frequency characteristic stored in the storage device 11 for each session of blood purification treatment and saving the stored impedance frequency characteristic as past impedance-frequency-characteristic data. Specifically, the saving device 14 according to the present embodiment is configured to successively store, for each session of blood purification treatment, the impedance frequency characteristic acquired by the calculating device 10 after the patient's blood is introduced into the arterial blood circuit 1a and the venous blood circuit 1b (after blood removal) and before the blood purification treatment is started, and to save the stored impedance frequency characteristic as past impedance-frequency-characteristic data.

The monitoring device 15 is electrically connected to the storage device 11 and to the saving device 14 and is capable of comparing the past impedance-frequency-characteristic data saved in the saving device 14 and the impedance frequency characteristic of the current session of blood purification treatment stored in the storage device 11, and monitoring any change in the frequency characteristic. As with the identification method employed by the identifying device 12 according to the above embodiment, the monitoring device 15 may employ another monitoring method in which correlation between the resistance component and the capacitance component of the impedance frequency characteristic is utilized (see Expressions 1 and 2).

The present embodiment employs the saving device 14 capable of successively storing the impedance frequency characteristic stored in the storage device 11 for each session of blood purification treatment and saving the stored impedance frequency characteristic as past impedance-frequency-characteristic data; and the monitoring device 15 capable of comparing the past impedance-frequency-characteristic data saved in the saving device 14 and the impedance frequency characteristic of the current session of blood purification treatment that is stored in the storage device 11, and monitoring any change in the frequency characteristic. Therefore, the state of the patient's vascular access (any occurrence of stenosis or the like) can be monitored, and any abnormal state of puncture into the blood vessel A (the vascular access) with the arterial puncture needle (a) or the venous puncture needle (b) that may occur before the current session of blood purification treatment is started can be identified.

Specifically, the impedance frequency characteristic stored in the storage device 11 is successively stored for each session of blood purification treatment and is saved as past impedance-frequency-characteristic data. Therefore, if an impedance frequency characteristic acquired before a new session of blood purification treatment is started is compared with the past impedance frequency characteristic and the change in the characteristic is monitored, stenosis in the patient's vascular access that may occur with time can be detected, or any abnormal state of puncture into the blood vessel A (the vascular access) with the arterial puncture needle a or the venous puncture needle b can be detected before the blood purification treatment is started.

While some embodiments have been described above, the present invention is not limited thereto. For example, the oscillating device 8 is not limited to the one that is capable of changing the frequency of the alternating current between a low frequency and a high frequency. The oscillating device 8 may be capable of changing the frequency among a plurality of frequencies in a low-frequency range or in a high-frequency range. Furthermore, in the present embodiment, the impedance frequency characteristic acquired by the calculating device 10 after the patient's blood is introduced into the arterial blood circuit 1a and the venous blood circuit 1b and before the blood purification treatment is started is stored in the storage device 11 and is taken as the frequency characteristic in the case of normal puncture into the blood vessel. Alternatively, a frequency characteristic acquired at another point of time (for example, at an early stage of the blood purification treatment, or when the state of normal puncture into the blood vessel with the puncture needles is identified) may be stored in the storage device 11 and taken as the frequency characteristic in the case of normal puncture into the blood vessel.

In addition, the identifying device 12 may be capable of comparing a frequency characteristic defined by the resistance component alone of the impedance acquired by the calculating device 10 and a frequency characteristic defined by the resistance component alone of the impedance stored in the storage device 11, and identifying whether the puncture into the patient's blood vessel with the arterial puncture needle (a) or the venous puncture needle (b) is normal in accordance with the change in the frequency characteristic. For example, as illustrated in FIG. 10, a frequency characteristic defined by the resistance component alone of the impedance in the case of normal puncture into the patient's blood vessel with the arterial puncture needle (a) and the venous puncture needle (b) is stored as P1 in the storage device 11, and a frequency characteristic defined by the resistance component of the impedance at each of different frequencies that is measured by the measuring device 9 is acquired as P2. Then, if the frequency characteristic P2 matches with the frequency characteristic P1, it is identified that the puncture is normal (the state of puncture is normal). If the two do not match, it is identified that needle dislodgement has occurred (the state of puncture is abnormal).

To summarize, the identifying device 12 is capable of comparing a frequency characteristic defined by the resistance component alone of the impedance acquired by the calculating device 10 and a frequency characteristic defined by the resistance component alone of the impedance stored in the storage device 11, and identifying whether the puncture into the patient's blood vessel with the arterial puncture needle (a) or the venous puncture needle (b) is normal in accordance with the change in the frequency characteristic. Therefore, the abnormal state of puncture into the blood vessel with the arterial puncture needle (a) or the venous puncture needle (b) can be easily identified in accordance with the resistance component alone.

Furthermore, elements such as the oscillating device 8, the measuring device 9, the calculating device 10, the storage device 11, and the identifying device 12 according to the present embodiment (in the other embodiment, the saving device 14 and the monitoring device 15 as well) that are provided in the apparatus body B may alternatively be provided in a device (such as a personal computer) separate from the apparatus body B. Moreover, the blood purification apparatus to which the present invention is applied is not limited to a hemodialysis apparatus and may be an apparatus intended for another kind of blood purification treatment.

The present invention is applicable to any blood purification apparatus, including those having different appearances, other additional functions, and so forth, as long as the blood purification apparatus includes an identifying device capable of comparing an impedance frequency characteristic acquired by a calculating device and an impedance frequency characteristic stored in a storage device, and identifying whether the puncture into a patient's blood vessel with an arterial puncture needle or a venous puncture needle is normal in accordance with the change in the frequency characteristic.

REFERENCE SIGN LIST 1 blood circuit
1a arterial blood circuit
1b venous blood circuit
2 dialyzer (blood purification device)
3 blood pump
4 air-trap chamber
5 bubble detection device
6 ultrafiltration pump
7 duplex pump
8 oscillating device
9 measuring device
10 calculating device
11 storage device
12 identifying device
13 informing device
14 saving device
15 monitoring device
D1 arterial electrode
D2 venous electrode
a arterial puncture needle
b venous puncture needle
B apparatus body
L1 dialysate introduction line
L2 dialysate drain line
R lock ring

The invention claimed is:

1. A blood purification apparatus comprising:
an arterial blood circuit provided with an arterial puncture needle at a distal end, the arterial puncture needle being stickable into a patient;
a venous blood circuit provided with a venous puncture needle at a distal end, the venous puncture needle being stickable into the patient; and
a blood purification device connected to a proximal end of the arterial blood circuit and to a proximal end of the venous blood circuit and being capable of purifying blood of a patient that extracorporeally circulates through the arterial blood circuit and the venous blood circuit,
the blood purification apparatus comprising:
an arterial electrode provided to the arterial blood circuit;
a venous electrode provided to the venous blood circuit;
an oscillating device capable of supplying, by applying a voltage between the arterial electrode and the venous electrode, an alternating current at a predetermined frequency to the blood of the patient through the arterial puncture needle and the venous puncture needle that are stuck in a blood vessel of a patient, the oscillating device being capable of changing a frequency of the alternating current among a plurality of frequencies;
a measuring device capable of measuring an impedance of a flow route supplied with the alternating current from the oscillating device, the impedance being measured for each of the plurality of frequencies;
a calculating device capable of acquiring an impedance frequency characteristic based on the impedances measured for each of a respective one of the plurality of frequencies by the measuring device;
a storage device capable of storing the impedance frequency characteristic acquired in a case of normal puncture into the blood vessel of the patient with the arterial puncture needle and the venous puncture needle; and
an identifying device capable of comparing the impedance frequency characteristic acquired by the calculating device and the impedance frequency characteristic stored in the storage device, and identifying whether a puncture into the blood vessel of the patient with the arterial puncture needle or the venous puncture needle is normal in accordance with a change in a frequency characteristic.

2. The blood purification apparatus according to claim 1, wherein the oscillating device is capable of changing the frequency of the alternating current between a low frequency and a high frequency.

3. The blood purification apparatus according to claim 1, wherein the storage device is capable of storing the impedance frequency characteristic acquired by the calculating device after the blood of the patient is introduced into the arterial blood circuit and the venous blood circuit and before blood purification treatment is started.

4. The blood purification apparatus according to claim 3, wherein a supply of the alternating current from the oscillating device with the frequency among the plurality of frequencies that is changed, acquisition of the impedance frequency characteristic by the calculating device, and an identification by the identifying device are each performed continuously or intermittently from a start to an end of the blood purification treatment.

5. The blood purification apparatus according to claim 3, further comprising:
a saving device capable of successively storing the impedance frequency characteristic stored in the storage device for each session of blood purification treatment and saving the stored impedance frequency characteristic as past impedance-frequency-characteristic data; and
a monitoring device capable of comparing the past impedance-frequency-characteristic data saved in the saving device and current impedance frequency characteristic of a current session of blood purification treatment that is stored in the storage device, and monitoring any change in the frequency characteristic.

6. The blood purification apparatus according to claim 1, further comprising an informing device that informs a result of an identification by the identifying device that the puncture into the blood vessel with the arterial puncture needle or the venous puncture needle is abnormal.

7. The blood purification apparatus according to claim 1, wherein the identifying device is capable of comparing the frequency characteristic defined by a resistance component alone of the impedance frequency characteristic acquired by the calculating device and a frequency characteristic defined by a resistance component alone of the impedance frequency characteristic stored in the storage device, and identifying whether the puncture into the blood vessel of the patient with the arterial puncture needle or the venous puncture needle is normal in accordance with the change in the frequency characteristic.

8. The blood purification apparatus according to claim 1, wherein the arterial electrode and the venous electrode are each an electrode formed in contact with an outer peripheral surface of a flexible tube forming a corresponding one of the arterial blood circuit and the venous blood circuit, and each allow the voltage to be non-wettably applied to liquid flowing in the corresponding one of the arterial blood circuit and the venous blood circuit.

* * * * *